United States Patent [19]
Cohen et al.

[11] Patent Number: 5,776,445
[45] Date of Patent: Jul. 7, 1998

[54] OPHTHALMIC DELIVERY SYSTEM

[75] Inventors: Smadar Cohen, Petach Tikva; Esther Lobel, Rehovot, both of Israel

[73] Assignees: Teva Pharmaceutical Industries Ltd., Netanya; The Ben Gurion University of the Negev, Beersheva, both of Israel

[21] Appl. No.: 689,218

[22] Filed: Aug. 7, 1996

Related U.S. Application Data

[63] Continuation of Ser. No. 262,294, Jun. 20, 1994, abandoned.

[51] Int. Cl.$^6$ .................... A61K 31/74; A61K 47/36
[52] U.S. Cl. .................... 424/78.04; 514/779; 514/912
[58] Field of Search .................... 424/78.04; 514/779, 514/912

[56] References Cited

U.S. PATENT DOCUMENTS

| | | | |
|---|---|---|---|
| 4,861,760 | 8/1989 | Mazuel et al. | 514/54 |
| 5,139,783 | 8/1992 | Handjani et al. | 424/401 |
| 5,144,016 | 9/1992 | Skjak-Braek et al. | 536/3 |
| 5,147,648 | 9/1992 | Bannert | 424/435 |
| 5,200,180 | 4/1993 | Bannert | 424/427 |
| 5,336,668 | 8/1994 | Francesco et al. | 514/23 |

FOREIGN PATENT DOCUMENTS

| | | |
|---|---|---|
| 0 357793 | 3/1990 | European Pat. Off. |
| 0 507224 | 10/1992 | European Pat. Off. |

OTHER PUBLICATIONS

"The Controlled Release of Prednisolone Using Alginate Gel"; S. Sugawara, T. Imai and M. Otagiri; *Pharmaceutical Research*, vol. 11, pp. 272–277, 1994.

"PS–60: A New Gel–Forming Polysaccharide"; R. Moorhouse, G.T. Colegrove, P.A. Sandford, J.K. Baird and K.S. Kang; *Solution Properties of Polysaccharides;* ACS Symposium Series 150; American Chemical Society, Washington, D.C.; pp. 111–124, 1981.

"Effect of poloxamer 407 gel on the miotic activity of pilocarpine nitrate in rabbits"; Susan C. Miller and Maureen D. Donovan; *International Journal of Pharmaceutics*, vol. 12, Nos. 2–3, pp. 147–152; 1982.

"Diffusional Systems for Controlled Release of Drugs to the Eye"; John W. Shell, Ph.D. and Richard W. Baker, Ph.D.; *Annals of Ophthalmology;* vol. 6, No. 10, pp. 1037–1045, Oct. 1974.

"Ocular Therapy With Nanoparticulate Systems For Controlled Drug Delivery"; Robert Gurny, Tor Boye and Houssam Ibrahim; *Journal of Controlled Release;* Special Issue, pp. 353–361, 1985.

"Gelrite: A novel, ion–activated, in–situ gelling polymer for ophthalmic vehicles. Effect on bioavailability of timolol"; A. Rozier, C. Mazuel, J. Grove and B. Plazonnet; *International Journal of Pharmaceutics;* vol. 57, No. 2, pp. 163–168, Dec. 22, 1989.

Olav Simsrod, "Molecular Basis for some Physical Properties of Alginates in the Gel State," *Faraday Discuss. Chem. Soc.*, vol. 57, 1974, pp. 263–281.

Ji et al., *Chemical Abstracts*, vol. 102, #21275.

*Primary Examiner*—Carlos Azpuru
*Attorney, Agent, or Firm*—Kenyon & Kenyon

[57] ABSTRACT

The present invention relates to formulations particularly well suited for use as delivery systems in the delivery of an active agent to the eye. The formulations comprise an alginate having a particular proportion of guluronic acid.

12 Claims, 8 Drawing Sheets

OPHTHALMIC DELIVERY SYSTEM

This application is a continuation of application Ser. No. 08/262,294 filed 20 Jun. 1994, now abandoned.

FIELD OF INVENTION

The present invention relates to a novel delayed release composition suitable for the release of active ingredients to a human or animal body, and especially well suited for the release of active ingredients via the ocular route.

BACKGROUND

Delivery of active agents to the eye has presented a problem to those skilled in the art. The problem arises, in part, because the site of delivery is essentially a non-static site. Various approaches have been developed to find a suitable medium within which to formulate an active ingredient so as to provide an effective delivery system for the active ingredient to the eye.

These approaches include the use of ointments, liquids and solid implants. Eye ointments may increase the residence time of ocular drugs but they are inconvenient to use, impair the vision by blurring and are therefore generally only recommended to be administered prior to going to sleep.

Extended corneal contact times, as well as sustained release, have been obtained with solid eye implants such as Ocusert™, a trademarked medication release system manufactured and sold by Alza Corporation, Palo Alto, Calif. The use of the Ocusert™ medication release system is described in the following article, Shell J W and Baker R W, (1974) Ann. Ophthalmol 6 1037–1047. However, solid implants possess a major disadvantage in that many patients find it difficult to tolerate the introduction of the solid object represented by this implant into the conjunctival culs-de-sacs of the eye.

Liquid vehicles for delivery of active ingredients to the eye have also been suggested. However, liquid vehicles generally suffer from the disadvantage that a large proportion of the liquid vehicle and hence the active agent administered is lost as a result of lacrimal drainage because the site of delivery to the eye is both fluid and mobile.

In an effort to overcome this problem and increase the total contact time of liquid vehicles, several groups have suggested the utilization of phase transition systems to deliver ophthalmic drugs at a controlled rate. Such systems may be applied to the eye in a liquid form and only once in the culs-de-sac will they shift to their gel phase.

Several such phase transfer systems have been reported. With the polymeric based system Poloxamer 407, described in Miller S C et al., (1982) Int J Pharm 12 147–152, solution viscosity increases when its temperature is raised to the eye temperature. In the cellulose acetophthalate (CAP) latex system, described in Gurney R et al. (1985) J Contr Release 2 353–361, the polymer coagulates when its native pH of 4.5 is raised by the tear fluid to pH 7.4. Both systems are characterized by a high polymer concentration (25% Poloxamer, 30% CAP) which is not well tolerated by the eye. In addition, the surfactive properties of the former and the low pH of the latter may be detrimental to ocular tolerance.

Another phase transition system is Gelrite™, a polysaccharide which forms clear gels in the presence of mono or divalent cations described in Moorhouse R et al. (1981) In "Solution Properties of Polysaccharides" pages 111–124 Ed. Brandt D A, Washington D.C. As described in Rozier A et al. (1989) Int J Pharm 57 163–168, in the conjunctival sac, this polymer changes from the liquid phase to the gel phase as a result of the ionic strength of the lacrimal fluid. Because it can form gels at low concentrations (~0.6% w/w), it is well tolerated by the eye.

One of the disadvantages of Gelrite™ is the incompatibility of Gelrite™ solutions with ionised formulation ingredients such as buffers, as the Gelrite™ solution will undergo premature phase transition. Therefore potential ion pair-forming agents have to be added and the total ionic strength of the formulation must be kept low.

Alginate is a block-copolymer containing two kinds of homopolymeric blocks, of β-D mannuronic acid (M-M) blocks and α-L-guluronic acid (G-G) blocks together with blocks with alternating sequence (M-G). As described in Simsrod, O (1974) Acta Chem Scan 28 263–281, the affinity of alginates for divalent metal ions increases with increasing content of L-guluronic acid residues in the alginates. Various alginates containing different proportions of guluronic and mannuronic acids have been used as dental impression materials, wound healing materials, as pharmaceutical excipients and in sustained release systems to the GI tract.

U.S. Pat. No. 5,200,180 describes pharmaceutical compositions for the treatment of the human eye which are formed by combining at least two components capable of gel formation with one another. One of the components may be an alginate and the other component is preferably a calcium salt. The composition may optionally additionally contain a therapeutic ingredient.

The two components capable of gel formation are dissolved separately from one another. The individual solutions are then applied successively or simultaneously to the eye whereupon gelation occurs and the resultant gel adheres to the eye, keeping it moist and also enabling drugs to be applied with lower frequency.

The disadvantage of the above method is the application of two separate preparations and the requirement of having to mix the two solutions upon administration at the proper volumes and the appropriate concentration ratio for gelling to occur. Frequently the solutions are diluted by tear fluid before gelation can occur.

SUMMARY OF THE INVENTION

The present invention advantageously provides a delivery formulation suitable for extending the duration of activity of an active agent administered to the eye.

We have discovered that particular alginates comprising a defined minimum proportion of guluronic acid pass into a gel phase when mixed with lacrimal fluid. The gelation of these alginates occurs without the successive or simultaneous addition of any other agents. Without wishing to be limited by theory, it is believed that the gelation occurs due to the particular alginates being sensitive to the calcium concentration in lacrimal fluid.

Accordingly the present invention includes a formulation comprising a therapeutically effective amount of at least one active agent together with an alginate whose composition comprises at least 50% guluronic acid. Prior to application to the eye, the formulation is preferably substantially non-gelled. After application to the eye and exposure to the lacrimal fluid, it is preferred that the formulation gel to an extent sufficient to maintain the presence of the therapeutically active agent in the ocular region.

The formulations of the present invention advantageously maintain the presence of an active agent in the eye, thus extending the effect of such active agent and reducing the frequency of drug administration. They are also easy to administer and are more comfortable to the user than many prior art formulations.

BRIEF DESCRIPTION OF THE DRAWINGS

FIG. 3a depicts baseline and mean treatment values. FIG. 3b depicts treatment values (means±SE (standard error)).

FIG. 4a depicts baseline and mean treatment values. FIG. 4b depicts treatment values (means±SE (standard error)).

FIG. 5a depicts baseline and mean treatment values. FIG. 5b depicts treatment values (means±SE (standard error)).

DESCRIPTION OF THE PREFERRED EMBODIMENTS

The formulations of the present invention comprise an alginate wherein the guluronic acid content is at least 50%, preferably at least 60%, more preferably at least 70%, and a therapeutically active agent.

The formulations of the present invention may alternatively be defined in terms of the proportion of mannuronic acid in the alginate. Thus, the present invention also relates to a controlled release formulation comprising a therapeutically effective amount of at least one active agent together with an alginate whose composition comprises no more than 50% mannuronic acid. Preferably, the alginate comprises no more than 40% mannuronic acid, more preferably no more than 30% mannuronic acid.

Preferably, the alginate utilized in the formulations of the present invention comprises from 50–95% guluronic acid and from 5–50% mannuronic acid.

It is also preferred that the formulations of the present invention are substantially non-gelled prior to contact with lacrimal fluid. Thus, in the formulation of the present invention the therapeutically active agent, and the alginate, are preferably dissolved and/or suspended in a pharmacologically safe solution prior to application. We have discovered that 0.5 to 5.0%, by weight, alginate may be utilized in the solution, together with the active agent, to permit the formulation to sufficiently gel upon contact with lacrimal fluid.

Suitable pharmacologically safe solutions include, but are not limited to the following: preservatives, tonicity agents, buffers as known in the art, or water for injection.

The formulations of the present invention are particularly advantageous when used to delivery therapeutic agents to the eye.

Those of ordinary skill in the art will readily appreciate that a wide variety of therapeutic agents may be formulated in the manner disclosed herein. Thus, the suggested agents given below are exemplary only and are not intended to limit the scope of the invention.

Therapeutic agents that are suitable for inclusion in the formulations of the present invention for opthalmic administration include, but are not limited to: glaucoma agents such as beta-adrenergic blockers such as timolol, betaxolol, levobunolol, metipranolol and carteolol; adrenergic agonists such as epinephrine, apraclonidine and related 2-substituted amino imidazolines; carbonic anhydrase inhibitors such as acetazolamide, methazolamide and aryl and heteroaryl sulphonamides; miotic cholinergic drugs such as pilocarpine and carbachol; dopamine agonists and antagonists; alpha-2 adrenergic agonists; anti-inflammatory agents, non-steroids such as diclofenac and ketorolac and steroids including, prednisolone acetate, tetrahydrocortisol; methotrexate and cyclosporines; antibiotics such as chloramphenicol, neomycin; anti-virals such as vidarabine, acyclovir and trifluorothymidine; anti-bacterials and anti-infectives such as aminoglycosides, quinolones such as ciprofloxacin and ofloxacin and beta-lactams such as cephalosporins; ACE inhibitors, anti-hypertensives, anti-cataract agents, antioxidants, anti-allergics, mast cell stabilizers such as sodium chromoglycate, growth factors such as EGF, FGF, PDGF and calcium channel blockers.

The formulations of the present invention may contain up to 50% of active agent, preferably 0.25–10% (w/v). The necessary amount of formulation to administer can then be calculated by the man skilled in the art. As set forth below, the formulations of the present invention may also be utilized in the absence of an active agent to treat conditions such as dry eye.

In addition to their usefulness in delivering therapeutic agents to the eye, the formulations of the present invention are also useful without a therapeutic agent for preventing dryness of the eye, a condition associated with dry eye syndrome. In this form, the formulations of the present invention are also useful in the treatment or prevention of other conditions of the eye associated with aging, smog, sport, systemic medication, clinical conditions such as Sjorgen's Syndrome, chemotherapy, collagen diseases or malnutrition.

Thus, the present invention further relates to a method of treating diseases of the eye comprising administering an alginate whose composition comprises at least 50% guluronic acid.

The formulations of the present invention may optionally further contain other ophthalmically acceptable agents including buffers, disinfectants, preservatives such as Thimerosal, chlorobutanol or paraben or tonicity agents such as sodium chloride and mannitol.

The usefulness and advantages of the present invention are further illustrated, and will become further apparent from the following examples. These examples are for illustrative purposes and are not intended to limit the scope of the invention.

EXAMPLE 1

The following procedure was utilized to test the effectiveness of the formulations of the present invention in comparison with other means for introducing active agents to the eye. In this Example the intraocular pressure (IOP) of normotensive albino rabbits was measured with a Modular Tonometer (Mentor) after the rabbits were treated with pilocarpine alone, or pilocarpine in an alginate formulation.

PROCEDURE

The rabbits were divided into two groups. The IOP was measured in both eyes of each rabbit at various times during the 24 hours prior to drug administration using topically applied local anesthetic (Benoxinate 0.4% Fischer Co.) to obtain a baseline reading.

50 microliters of pilocarpine in an acetate buffer (pH 5.0) was administered into the conjunctiva of one eye of each rabbit within the first treatment group. The pilocarpine percentage of the solution is shown in Table 1 below. In the second treatment group, four alginates were utilized to prepare delivery formulations by incorporating 1.0% or 1.5%, by weight, of the alginate in 50 microliters of pilocarpine in an acetate buffer (pH 5.0).

The alginates utilized were as follows:

| Alginate | % guluronic acid | % mannuronic acid | Source |
|---|---|---|---|
| Ag1 | 40–50 | 50–60 | LF200B |
| Ag2 | 65–70 | 30–35 | MANUGEL DMB |
| Ag3 | 35–40 | 60–65 | KELTONE LV |
| Ag4 | 65–75 | 25–35 | SF120 |

LF200B alginate and SF120 alginate were both obtained from Pronova Biopolymer. MANUGEL DMB alginate and KELTONE LV alginate were both obtained from Kelco International, Waterford, Tadworth, Surrey KT20 5HQ, United Kingdom.

A drop of each pilocarpine/alginate formulation was administered to one eye of each rabbit in the second treatment group. The pilocaipine percentage of the formulation is shown in Table 1 below.

IOP measurements were taken for both eyes of each rabbit over the following 24 hour period.

RESULTS

The results of the various procedures are shown graphically in FIGS. 1–6. The treatments relating to each Figure is summarized in Table 1 below.

TABLE 1

| FIG. No. | PILOCARPINE % | FORMLATION | n |
|---|---|---|---|
| 1 | 2 | — | 6 |
| 1 | 2 | 1% Ag1 | 6 |
| 2 | 2 | — | 3 |
| 2 | 2 | 1.5% Ag2 | 3 |
| 3 (a & b) | 4 | — | 6 |
| 3 (a & b) | 4 | 1.5% Ag2 | 6 |
| 4 (a & b) | 2 | — | 8 |
| 4 (a & b) | 2 | 1% Ag2 | 8 |
| 5 (a & b) | 2 | — | 19 |
| 5 (a & b) | 2 | 1% Ag3 | 19 |
| 6 | 2 | — | 6 |
| 6 | 2 | 1% Ag4 | 6 |

Figure 1:
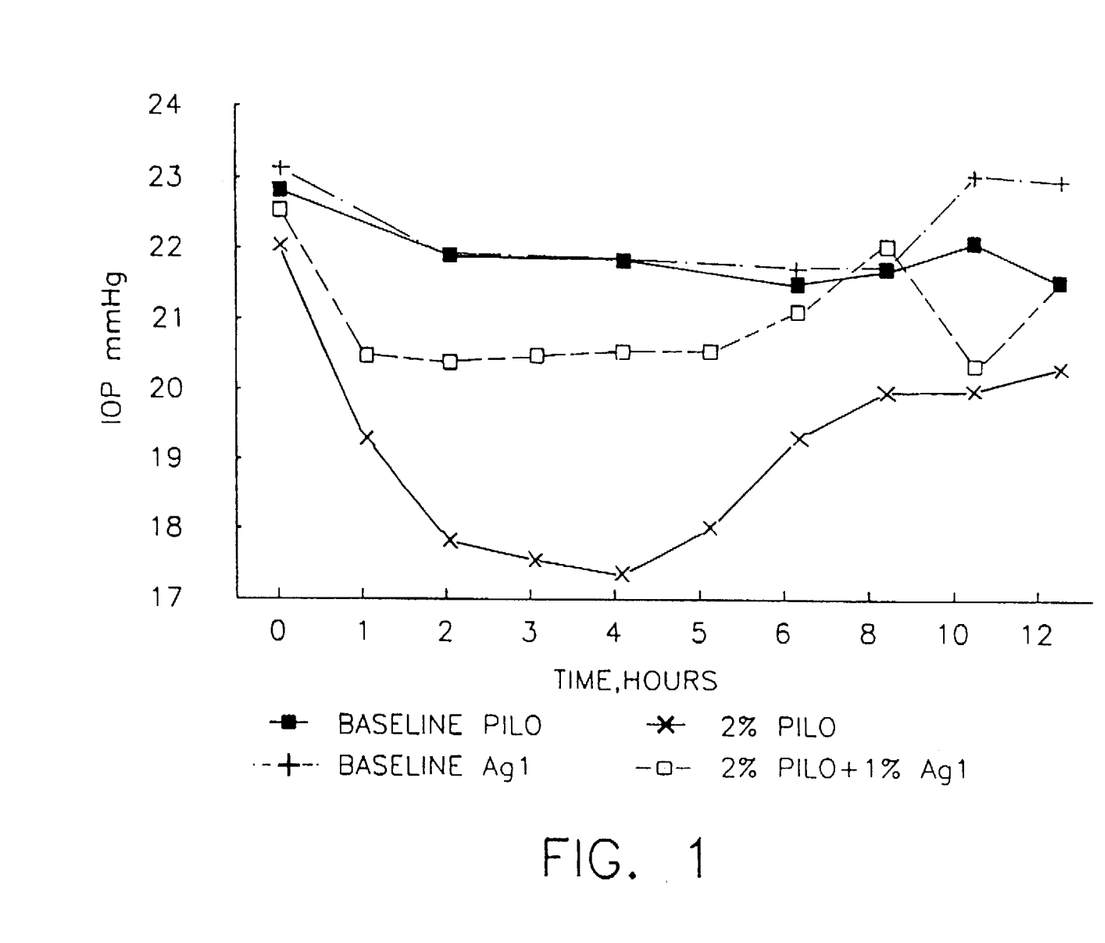
FIG. 1 is a graphical depiction of the results of the experiment described in Example 1 herein depicting the intraocular pressure (IOP) of normotensive albino rabbits before and after treatment with a 2% pilocarpine solution and a particular delivery formulation of the present invention, incorporating Ag1, described in Example 1.

FIG. 1 shows intraocular pressure (IOP) before and after treatment with pilocarpine and pilocarpine in combination with 1% Ag1, an alginate having a guluronic acid percentage below that specified for the alginate formulations used in the present invention. In particular, FIG. 1 depicts the mean baseline values for six rabbits, for pilocarpine (without carrier) and mean baseline values for six rabbits, for the Ag1 formulation without pilocarpine. The term baseline is utilized to the series of IOP measurements taken at specified time intervals. FIG. 1 also depicts the mean values of IOP for six rabbits after treatment with a 2% pilocarpine solution and the formulation comprising 2% pilocarpine and 1% Ag1. As shown in FIG. 1, the duration of the pressure reducing effect of pilocarpine was not extended by the formulation comprising 2% pilocarpine and 1% Ag1 as compared to 2% pilocarpine alone.

FIGS. 2, 3a, 3b, 4a and 4b clearly show that the duration of the pressure reducing effect of pilocarpine was extended in the formulations of the present invention incorporating Ag2, an alginate having a guluronic acid percentage of at least 50%.

Figure 2:
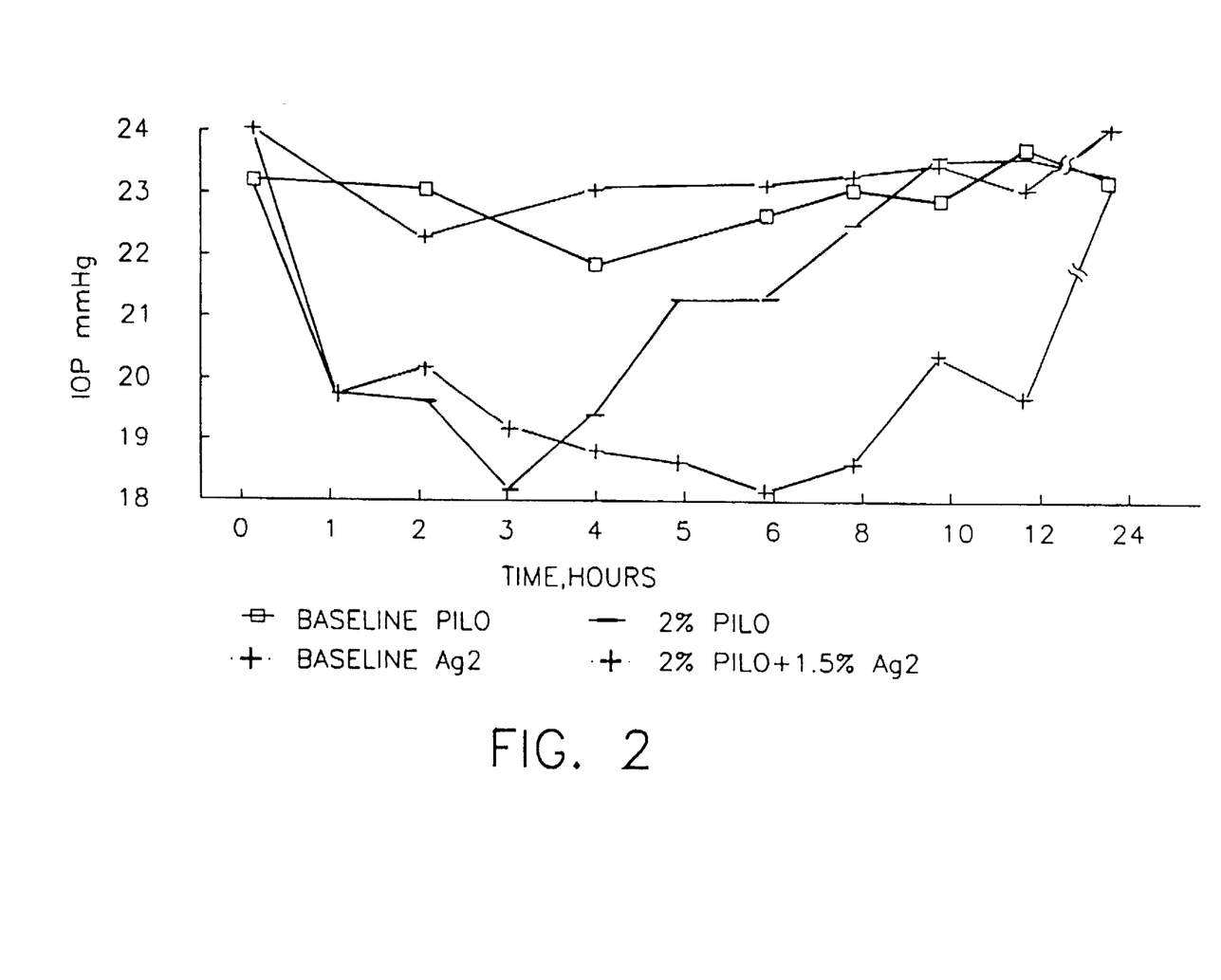
FIG. 2 is a graphical depictions of the results of the experiment described in Example 1 herein depicting the intraocular pressure (IOP) of normotensive albino rabbits before and after treatment with a 2% pilocarpine solution and a particular delivery formulation of the present invention, incorporating Ag2, described in Example 1.

FIG. 2 shows intraocular pressure (IOP) before and after treatment with pilocarpine and pilocarpine in combination with 1.5% Ag2, a formulation of the present invention. In particular, FIG. 2 depicts the mean baseline values for three rabbits, for pilocarpine (without carrier) and mean baseline values for three rabbits, for the Ag2 formulation without pilocarpine. FIG. 2 also depicts the mean values of IOP for three rabbits after treatment with a 2% pilocarpine solution and the formulation of the present invention comprising 2% pilocarpine and 1.5% Ag2. As shown in FIG. 2, the duration of the pressure reducing effect of pilocarpine was extended, in comparison with the baseline values, and in comparison to the solution incorporating 2% pilocarpine alone, after treatment with the formulation of the present invention incorporating 2% pilocarpine and 1.5% Ag2.

Figure 3A:
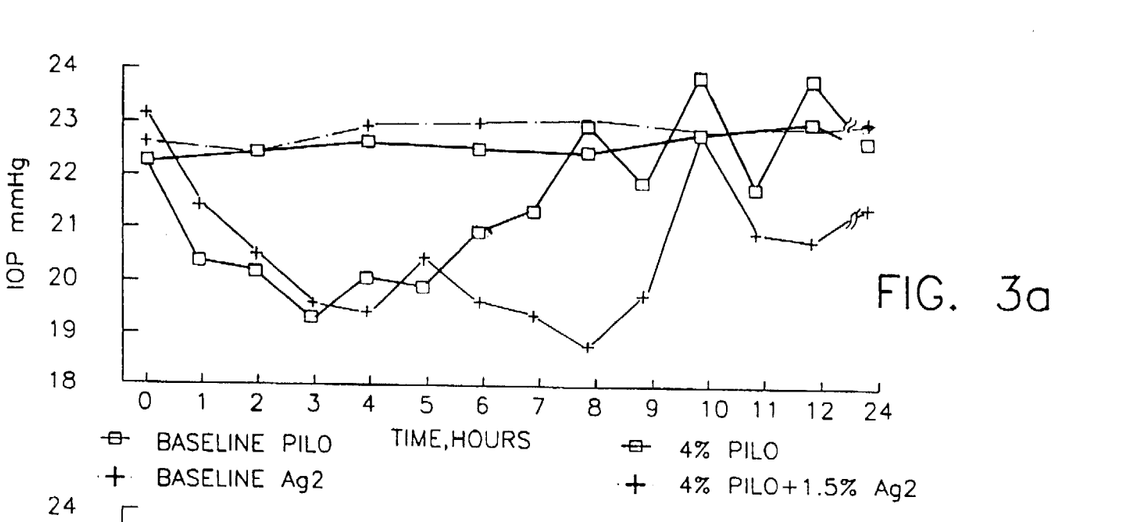
FIGS. 3a and 3b are graphical depictions of the results of the experiment described in Example 1 herein depicting the intraocular pressure (IOP) of normotensive albino rabbits before and after treatment with a 4% pilocarpine solution and a particular delivery formulation of the present invention, incorporating Ag2, described in Example 1.
Figure 3B:
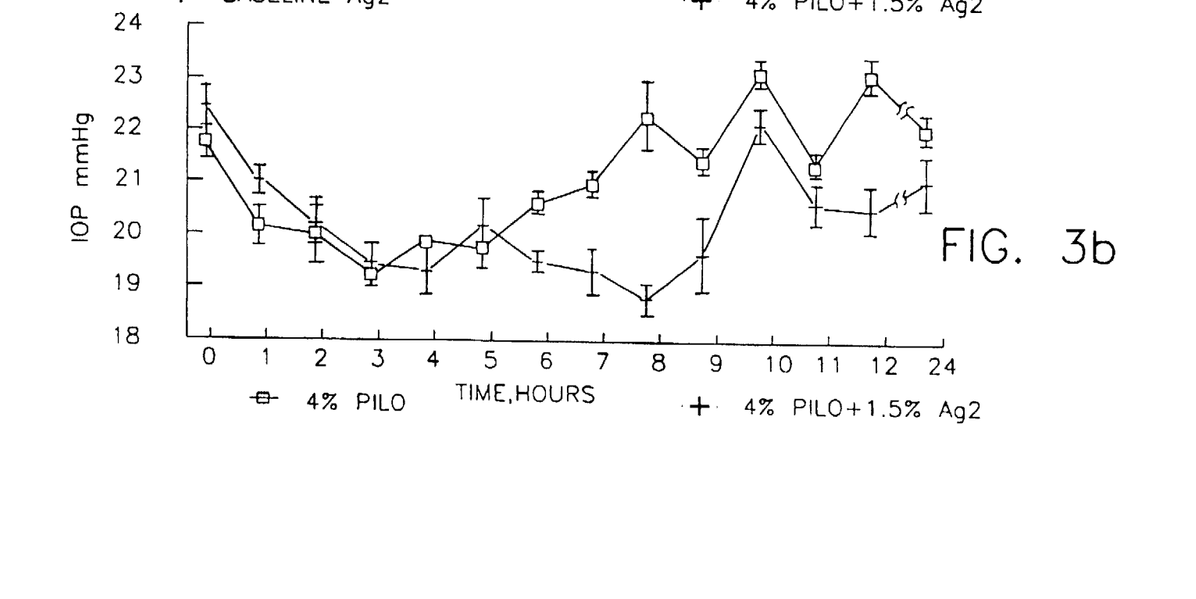

FIGS. 3a & 3b show intraocular pressure (IOP) before and after treatment with pilocarpine and pilocarpine in combination with Ag2, a formulation of the present invention. In particular, FIG. 3a depicts the mean baseline values for six rabbits, for pilocarpine (without carrier) and mean baseline values for six rabbits, for the Ag2 formulation without pilocarpine. FIG. 3a also depicts the mean values of IOP for six rabbits after treatment with a 4% pilocarpine solution and the formulation of the present invention comprising 4% pilocarpine and 1.5% Ag2. FIG. 3b depicts the mean±standard error (SE) of the treatment values for the treatment with the 4% pilocarpine solution and the formulation of the present invention comprising 4% pilocarpine and 1.5% Ag2 shown in FIG. 3a. As shown in FIGS. 3a and 3b, the duration of the pressure reducing effect of pilocarpine was extended, in comparison with the baseline values, and in comparison to the solution incorporating 4% pilocarpine alone, after treatment with the formulation of the present invention incorporating 4% pilocarpine and 1.5% Ag2.

Figure 4A:
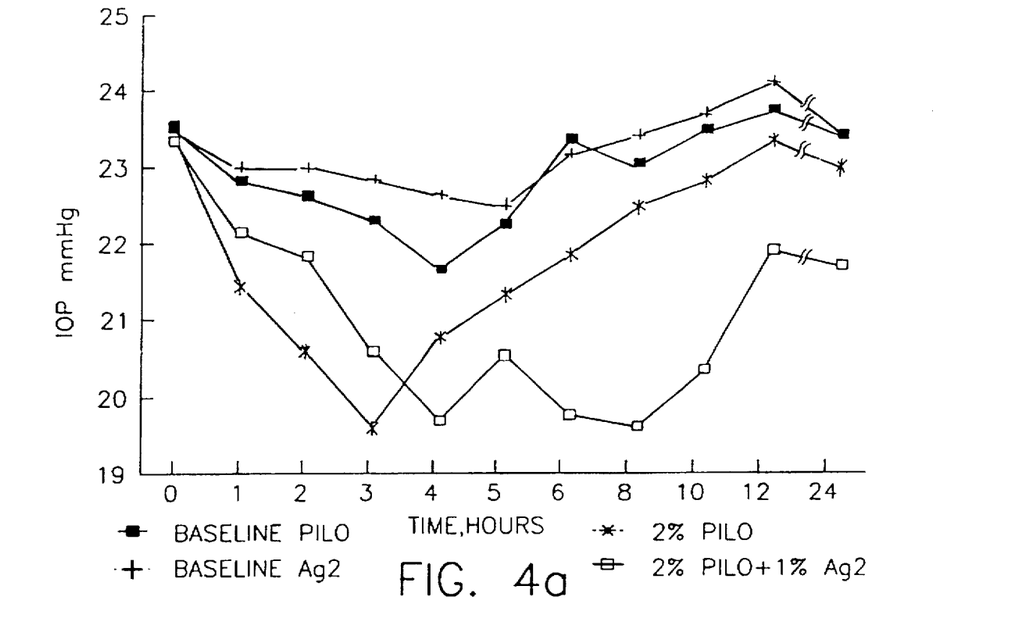
FIGS. 4a and 4b are graphical depictions of the results of the experiment described in Example 1 herein depicting the intraocular pressure (IOP) of normotensive albino rabbits before and after treatment with a 2% pilocarpine solution and a particular delivery formulation of the present invention, incorporating Ag2, described in Example 1.
Figure 4B:
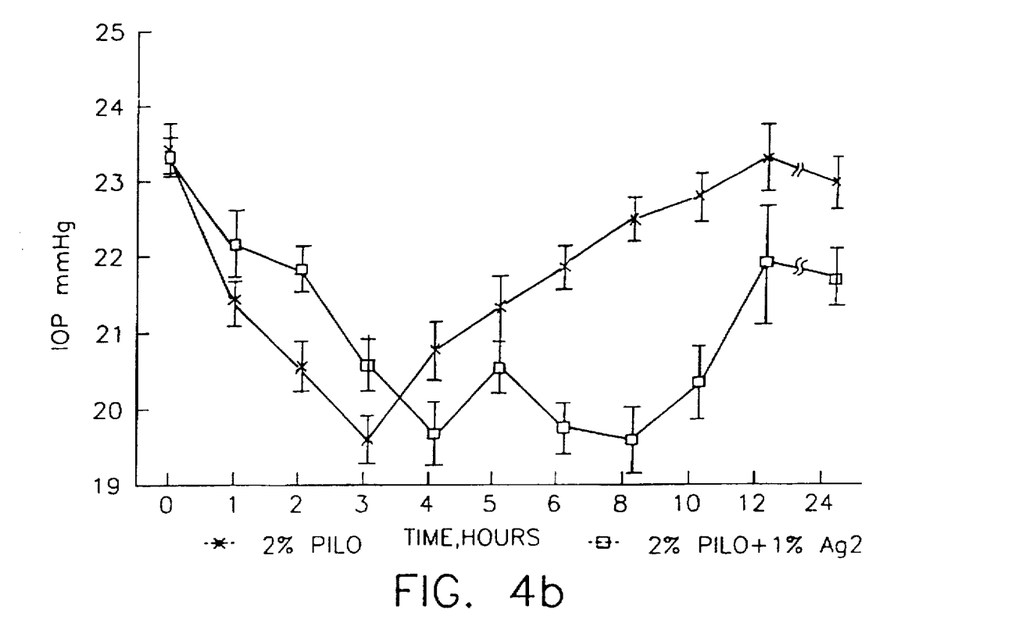

FIGS. 4a & 4b show intraocular pressure (IOP) before and after treatment with pilocarpine and pilocarpine in combination with Ag2, a formulation of the present invention. In particular, FIG. 4a depicts the mean baseline values for eight rabbits, for pilocarpine (without carrier) and mean baseline values for eight rabbits, for the Ag2 formulation without pilocarpine. FIG. 4a also depicts the mean values of IOP for six rabbits after treatment with a 2% pilocarpine solution and the formulation of the present invention comprising 2% pilocarpine and 1% Ag2. FIG. 4b depicts the mean±standard error (SE) of the treatment values for the treatment with the 2% pilocarpine solution and the formulation of the present invention comprising 2% pilocarpine and 1% Ag2 shown in FIG. 4a. As shown in FIGS. 4a and 4b, the duration of the pressure reducing effect of pilocarpine was extended, in comparison with the baseline values, and in comparison to the solution incorporating 2% pilocarpine alone, after treatment with the formulation of the present invention incorporating 2% pilocarpine and 1% Ag2.

Figure 5A:
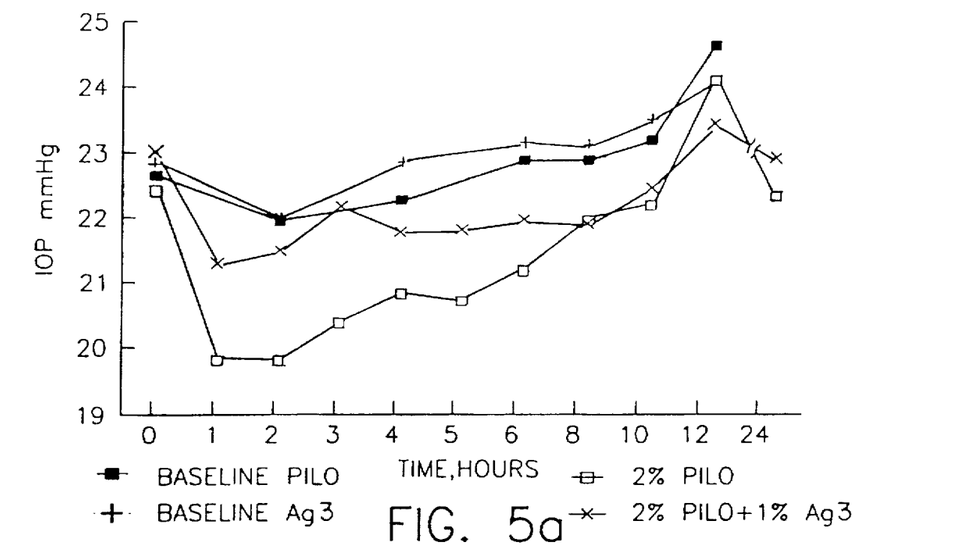
FIGS. 5a and 5b are graphical depictions of the results of the experiment described in Example 1 herein depicting the intraocular pressure (IOP) of normotensive albino rabbits before and after treatment with a 2% pilocarpine solution and a particular delivery formulation of the present invention, incorporating Ag3, described in Example 1.
Figure 5B:
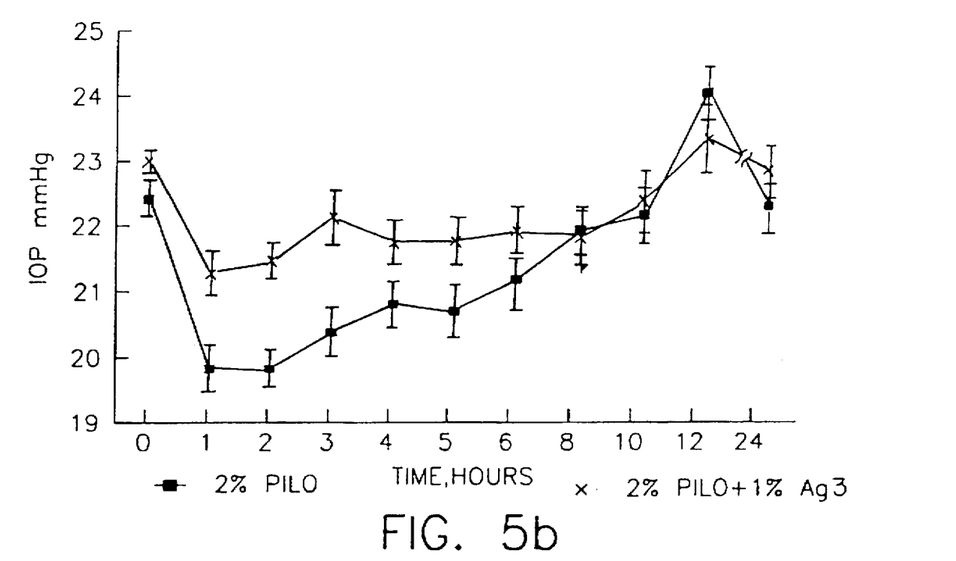

FIGS. 5a & 5b show intraocular pressure (IOP) before and after treatment with pilocarpine and pilocarpine in combination with Ag3, an alginate having a guluronic acid percentage below that specified for the alginate formulations used in the present invention. In particular, FIG. 5a depicts the mean baseline values for nineteen rabbits, for pilocarpine (without carrier) and mean baseline values for eight rabbits, for the Ag3 formulation without pilocarpine. FIG. 5a also depicts the mean values of IOP for nineteen rabbits after treatment with a 2% pilocarpine solution and the formulation of the present invention comprising 2% pilocarpine and 1% Ag3. FIG. 5b depicts the mean±standard error (SE) of the treatment values for the treatment with the 2% pilocarpine solution and the formulation comprising 2% pilocarpine and 1% Ag3 shown in FIG. 5a. As shown in FIGS. 5a and 5b, the duration of the pressure reducing effect of pilocarpine was not extended by the formulation comprising 2% pilocarpine and 1% Ag3 as compared to 2% pilocarpine alone.

Figure 6:
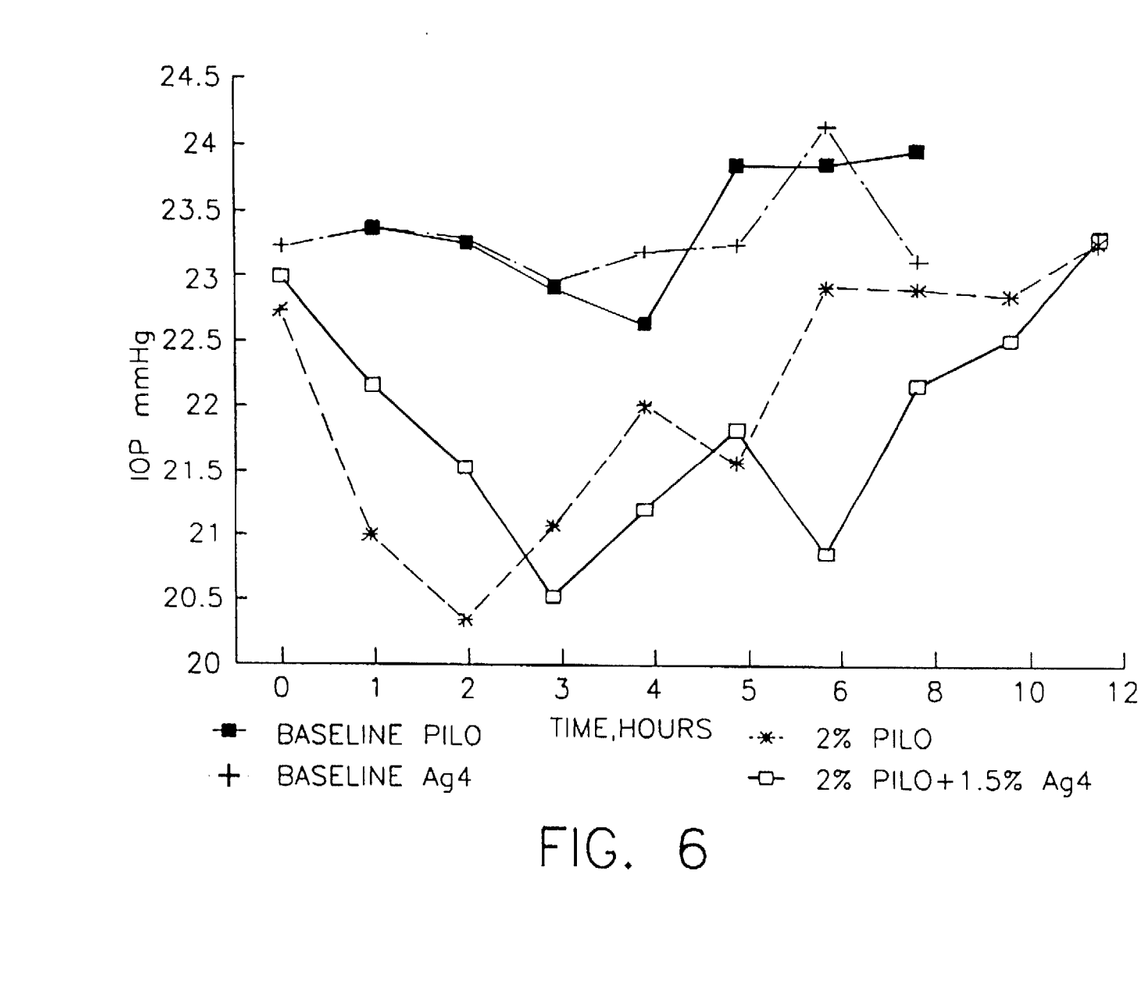
FIG. 6 is a graphical depiction of the results of the experiment described in Example 1 herein depicting the intraocular pressure (IOP) of normotensive albino rabbits before and after treatment with a 2% pilocarpine solution and a particular delivery formulation of the present invention, incorporating Ag4, described in Example 1.

FIG. 6 illustrates the effect of the formulation of the present invention incorporating Ag4, an alginate having a guluronic acid percentage of at least 50%. FIG. 6 shows intraocular pressure (IOP) before and after treatment with pilocarpine and pilocarpine in combination with 1.5% Ag4, a formulation of the present invention. In particular, FIG. 6 depicts the mean baseline values for six rabbits, for pilocarpine (without carrier) and mean baseline values for six rabbits, for the Ag4 formulation without pilocarpine. FIG. 6 also depicts the mean values of IOP for six rabbits after treatment with a 2% pilocarpine solution and the formulation of the present invention comprising 2% pilocarpine and 1.5% Ag4. As shown in FIG. 6, the duration of the pressure reducing effect of pilocarpine was extended, in comparison with the baseline values, and in comparison to treatment with 2% pilocarpine alone, after treatment with the formulation of the present invention incorporating 2% pilocarpine and 1.5% Ag4.

Figure 7:
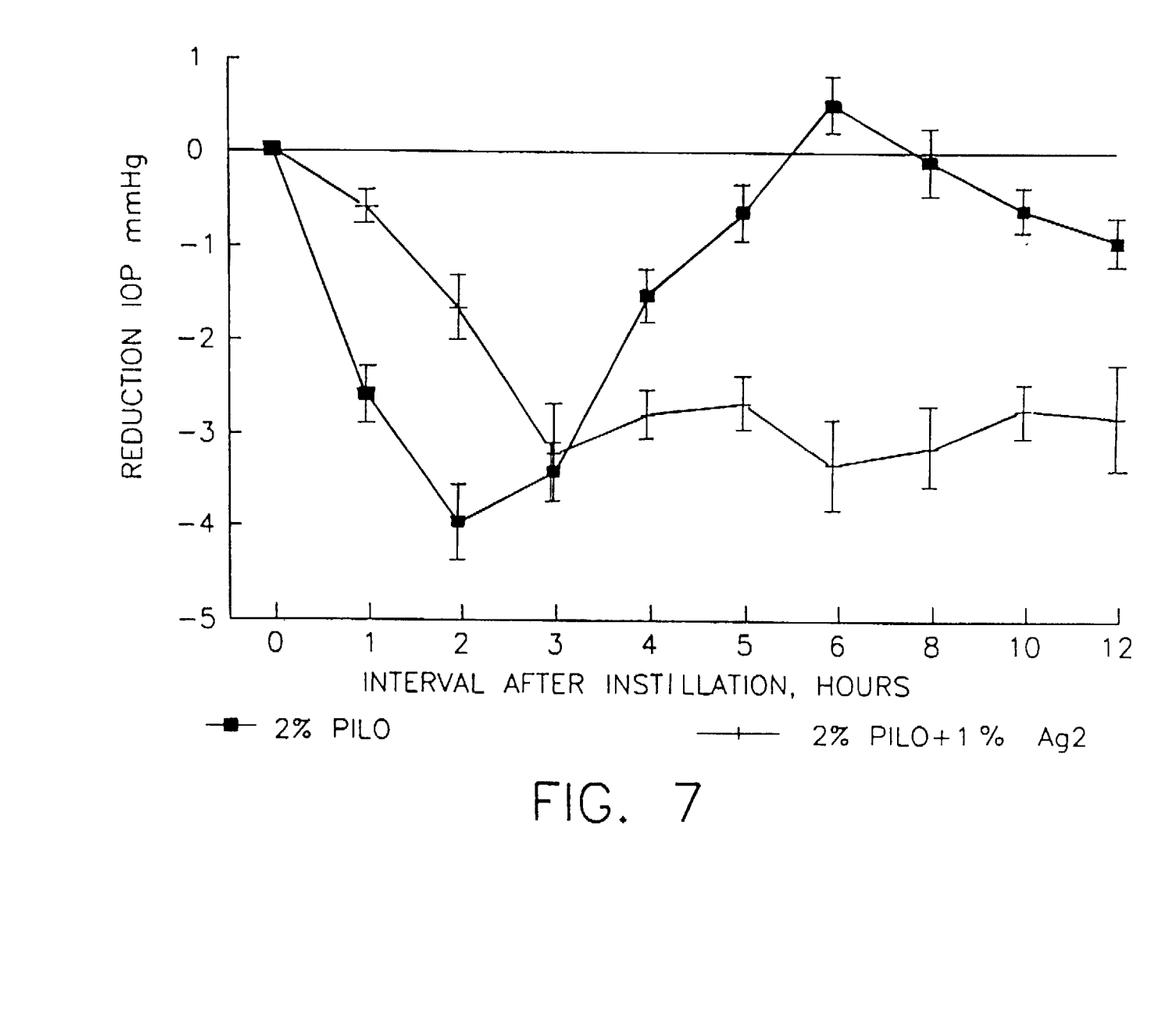
FIG. 7 is a graphical depiction of the results of the experiment described in Example 1 herein depicting the reduction of intraocular pressure (IOP) of normotensive albino rabbits from baseline values after treatment with a 2% pilocarpine solution and a particular delivery formulation of the present invention, incorporating Ag2, described in Example 1.

FIG. 7 is a representative graph showing the difference in IOP between pretreatment (baseline) values and the mean values±standard error for eyes treated with 2% pilocarpine alone and a formulation of the present invention incorporating 2% pilocarpine and 1% Ag 2. As shown in FIG. 7, the duration of the pressure reducing effect of pilocarpine was extended in eyes treated with the formulation of the present invention incorporating 2% pilocarpine and 1% Ag2, in comparison with the baseline values, and in comparison to treatment with 2% pilocarpine alone.

As a whole, these results illustrate that formulations of the present invention incorporating alginates having a guluronic acid percentage of at least 50%, as in the present invention, are of use in controlled release formulations for the eye. Alginates containing a lower percentage of guluronic acid did not provide a significant delay in the release of pilocarpine as can be seen from FIGS. 1 and 5 (a & b), and therefore would be of less use.

EXAMPLE 2

The experiment described in Example 1 was repeated using epinephrine in 1% Ag2 (MANUGEL DMB), a formulation of the present invention. The results are depicted graphically in FIG. 8.

Figure 8:
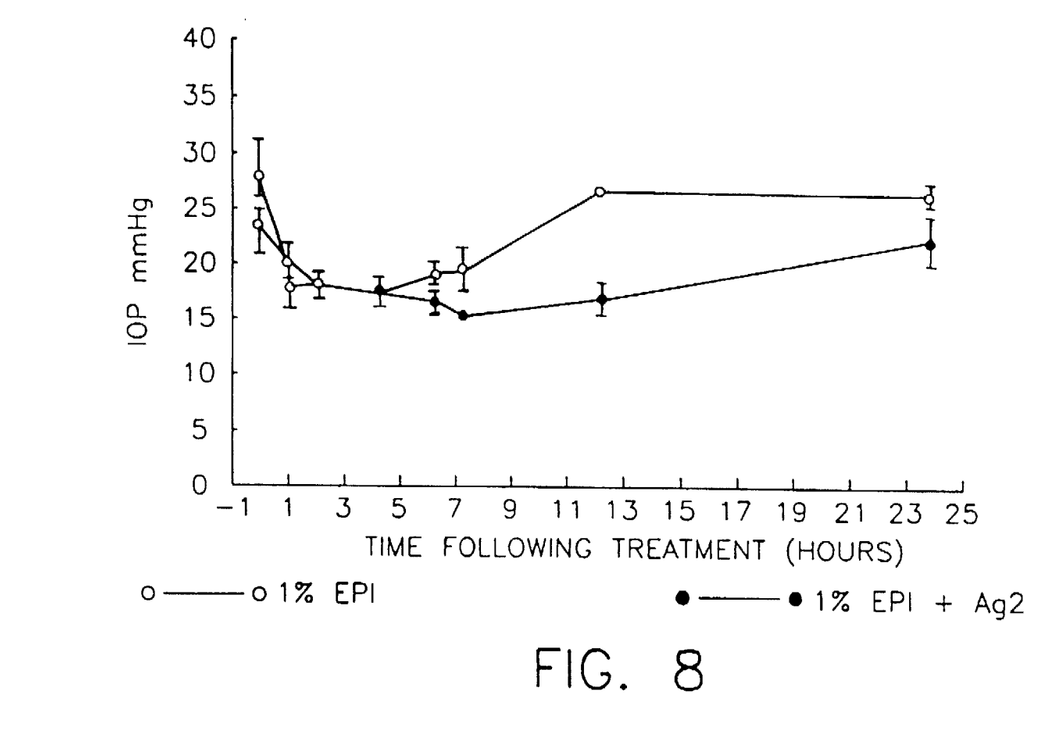
FIG. 8 is a graphical depiction of the results of the experiment described in Example 2 herein depicting the intraocular pressure (IOP) of normotensive albino rabbits before and after treatment with a 1% ephinephrine solution and a particular delivery formulation of the present invention, incorporating Ag2, described in Example 2.

FIG. 8 is a representative graph showing the difference in IOP between pretreatment (baseline) values and the mean values±standard error for eyes treated with 1% epinephrine alone and a formulation of the present invention incorporating 1% epinephrine and 1% Ag 2. As shown in FIG. 8, a significant delay and increase in the duration of pressure reduction was observed in eyes treated with the formulation of the present invention incorporating 1% epinephrine and 1% Ag2, in comparison to treatment with 1% epinephrine alone.

As can be seen, a significant delay and increase in the duration of pressure reduction was observed.

EXAMPLE 3

A further experiment, similar to the experiment described in Example 1, was performed with Ag4, sodium alginate SF120 (65–75% guluronic acid), in a formulation of the present invention which also included florescein. The florescein was visible for a much longer period of time in the rabbit eyes, using the high guluronic acid containing alginate solution.

EXAMPLE 4

Conventional laboratory methods, including filtering the alginate through a 0.45 μm filter, were utilized to produce a formulation of the present invention having the following composition:

| Ingredient | % w/w |
| --- | --- |
| Chlorbutanol BP | 0.5 |
| Sodium Chloride USP | 0.41 |
| Sodium Alginate MANUGEL DMB Eur. Ph. | 1.0 |
| Pilocarpine Nitrate BP/USP | 2.0 |
| Water for Injection q.s. | remainder |

EXAMPLE 5

Conventional laboratory methods, including filtering the alginate through a 0.45 μm filter, were utilized to produce a formulation of the present invention having the following composition:

| Ingredient | % w/w |
|---|---|
| Thimerosal BP | 0.5 |
| Sodium Chloride USP | 0.41 |
| Sodium Alginate MANUGEL DMB Eur. Ph. | 1.0 |
| Pilocarpine Nitrate BP/USP | 2.0 |
| Water for Injection q.s. | remainder |

It should be clearly understood that the forms of the present invention herein described are illustrative only and are not intended to limit the scope of the invention.

We claim:

1. An ophthalmic formulation comprising:
   a therapeutically effective amount of at least one active agent, and 0.5 to 5 weight percent of a dissolved sodium alginate comprising at least 50% guluronic acid,
   said sodium alginate undergoing a change from a dissolved phase to a gel phase upon contacting lacrimal fluid.

2. The ophthalmic formulation of claim 1, wherein the sodium alginate comprises at least 60% guluronic acid.

3. An ophthalmic formulation comprising:
   a therapeutically effective amount of at least one active agent, and 0.5 to 5 weight percent of a dissolved sodium alginate whose composition comprises no more than 50% mannuronic acid, said sodium alginate undergoing a change from a dissolved phase to a gel phase upon contacting lacrimal fluid.

4. The ophthalmic formulation of claim 3, wherein the sodium alginate comprises no more than 40% mannuronic acid.

5. The ophthalmic formulation of claim 1, wherein the sodium alginate comprises from 50–95% guluronic acid and from 5–50% mannuronic acid.

6. The ophthalmic formulation of claim 1 wherein at least one of the active agents is a therapeutic agent for the eye.

7. The ophthalmic formulation of claim 1, wherein active agents are selected from the group consisting of: a glaucoma agent, an anti-inflammatory agent, an anti-bacterial agent, an anti-viral agent and an anti-cataract agent.

8. The ophthalmic formulation of claim 1, wherein active agents are selected from the group consisting of: a beta-adrenergic blocker, a cholinergic agent, an alpha-adrenergic agonist and a steriodal or a non-steroidal anti-inflammatory agent.

9. The ophthalmic formulation of claim 1, wherein active agents are selected from the group consisting of pilocaipine. acyclovir, epinephrine, ciprofloxacin, sodium chromoglycate, dexamethasone and timolol.

10. A method of treating diseases of the eye comprising:
    administering a controlled release ophthalmic formulation to the eye, said ophthalmic formulation comprising:
    a therapeutically effective amount of at least one active agent, and 0.5 to 5 weight percent of a dissolved sodium alginate comprising at least 50% guluronic acid, said sodium alginate undergoing a change from a dissolved phase to a gel phase after administering to the eye and contacting lacrimal fluid.

11. The method of claim 10, wherein the sodium alginate comprises at least 60% guluronic acid.

12. A method of treating diseases of the eye comprising:
    administering a controlled release ophthalmic formulation to the eye, said ophthalmic formulation comprising:
    0.5 to 5 weight percent of a dissolved sodium alginate comprising at least 50% guluronic acid, said sodium alginate undergoing a change from a dissolved phase to a gel phase after administering to the eye and contacting lacrimal fluid.

* * * * *